(12) United States Patent
Feldman et al.

(10) Patent No.: US 8,488,117 B2
(45) Date of Patent: Jul. 16, 2013

(54) INSPECTION SYSTEM AND METHOD FOR FAST CHANGES OF FOCUS

(75) Inventors: Haim Feldman, Nof-Avalon (IL); Boris Morgenstein, Tel-Aviv (IL); Roman Naidis, Rehovot (IL); Adam Baer, Kfar Uriyah (IL)

(73) Assignee: Applied Materials Israel, Ltd., Rehovot (IL)

( * ) Notice: Subject to any disclaimer, the term of this patent is extended or adjusted under 35 U.S.C. 154(b) by 16 days.

(21) Appl. No.: 13/224,096

(22) Filed: Sep. 1, 2011

(65) Prior Publication Data

US 2012/0086937 A1    Apr. 12, 2012

Related U.S. Application Data

(60) Provisional application No. 61/391,672, filed on Oct. 10, 2010.

(51) Int. Cl.
*G01N 21/00* (2006.01)

(52) U.S. Cl.
USPC ........................................ 356/237.2

(58) Field of Classification Search
USPC ........................................ 356/237.2
See application file for complete search history.

(56) References Cited

U.S. PATENT DOCUMENTS 6,950,245 B2 * 9/2005 Nishioka et al. .............. 359/721
7,808,730 B2 * 10/2010 Yoon ............................ 359/826

* cited by examiner

*Primary Examiner* — Tu Ngyuen
(74) *Attorney, Agent, or Firm* — Kilpatrick Townsend & Stockton LLP

(57) ABSTRACT

An inspection system includes a first focusing unit configured to perform fast focus changes to a first focusing function applied to an incident light beam. A traveling lens acousto-optic device is arranged to receive the light beam focused by the first focusing function and produce focused spots using a plurality of traveling lenses generated in response to radio frequency signals. The traveling lenses apply a second focusing function and the traveling lens acousto-optic device is arranged to alter the second focusing function at a fast rate. The inspection system also includes optics arranged to direct the focused spots onto an inspected object and to direct radiation from the inspected object to a sensor.

18 Claims, 17 Drawing Sheets

1200

1300

1400

Receiving a first light beam through an input facet of a core made of ultraviolet durable material; wherein refractive indices of the core are responsive to an electric field applied on the core.
2010

Inducing, by a first set of electrodes that is connected to a first facet of the core that differs from the input facet, an electrical field having a magnitude that has a substantially parabolic shape along a first direction thereby causing the core to apply a first focusing function along the first direction on the first light beam; wherein the first direction is oriented to a propagation direction of the first light beam.
2020

Performing a fast change in the electrical field induced by the first set of electrodes thereby performing fast changes in the first focusing function. The change is fast as it is faster (and even much faster) than a change of focus that required moving (elevating or lowering) the inspected object, the optics and the like.
2030

INSPECTION SYSTEM AND METHOD FOR FAST CHANGES OF FOCUS

RELATED APPLICATIONS

This is a NONPROVISIONAL of, claims priority to and incorporates by reference U.S. Provisional Application 61/391,672, filed 10 Oct. 2010.

FIELD OF THE INVENTION

The invention relates to an inspection system and a method for fast changes of focus.

BACKGROUND OF THE INVENTION

Modern manufacturing processes are capable of producing objects that have nano-metric structural elements. Such inspected objects may be semiconductor wafers, reticles, solar panels and the like. An inspected surface of such an inspected object is not flat and this may result in focus errors.

Slowly developed focus errors can be compensated for by a mechanical module that can elevate or lower the inspected object. This compensation is relatively slow and is limited by mechanical constraints.

There is a growing need to provide a fast focus error correction method and an inspection system having fast focus alteration capabilities.

SUMMARY

An inspection system may be provided and may include a sensor; a mechanical module arranged to alter a distance between an inspected object and the sensor at a rate that is lower than a first rate; a first focusing unit arranged to receive a first beam and to apply a first focusing function along a first direction to provide a second beam, wherein the first focusing unit is arranged to alter the first focusing function at a rate that exceeds the first rate; a traveling lens acousto-optic device arranged to generate a plurality of traveling lenses in response to radio frequency signals, wherein each traveling lens is arranged to receive at least a portion of the second beam and to apply a second focusing function along a second direction to generate a plurality of focused spots and the traveling lens acousto-optic device is arranged to alter the second focusing function at a rate that exceeds the first rate; and optics arranged to direct the plurality of focused spots on the inspected object and to direct radiation from the inspected object to the sensor.

A focusing unit may be provided and may include a core having multiple facets, wherein refractive indices of the core are responsive to an electric field applied on the core and the core is made of ultra violet durable material; a first set of electrodes coupled to a first facet of the core; a second set of electrodes coupled to a second facet of the core, wherein when the electrodes induce an electrical field having a magnitude that has a substantially parabolic shape along a first direction, the core applies a first focusing function along the first direction on a first light beam, the first direction being oriented to a propagation direction of the first light beam; wherein the first light beam enters the core through an input facet of the core, wherein the input facet of the core that differs from the first and second facets; and wherein fast changes in the electrical field result in fast changes in the first focusing function.

A method for focus correction may be provided. The method may include receiving a desired focus error correction measure and altering, at a rate that exceeds a first rate and in response to the desired focus error correction measure, at least one focusing function out a first focusing function and a second focusing function; wherein the first rate is faster than a rate of distance alteration applied by a mechanical module arranged to alter the distance between an inspected object and a sensor; wherein the first focusing function is applied along a first direction by a first focusing unit; wherein the second focusing function is applied by a traveling lens acousto-optic device that is arranged to generate a plurality of traveling lenses in response to radio frequency signals; and wherein each traveling lens is arranged to receive at least a portion of the second beam and to apply the second focusing function along a second direction to generate a plurality of focused spots.

A method may be provided. The method may include altering, by a mechanical module, a distance between an inspected object and a sensor at a rate that is lower than a first rate; receiving, by a first focusing module, a first beam and applying a first focusing function along a first direction to provide a second beam; generating, by a traveling lens acousto-optic device, a plurality of traveling lenses in response to radio frequency signals; receiving, by each traveling lens at least a portion of the second beam; applying, by each traveling lens, a second focusing function along a second direction to generate a plurality of focused spots; directing the plurality of focused spots on the inspected object; directing radiation from the inspected object to a sensor; sensing radiation that impinges on the sensor; altering the first focusing function at a rate that exceeds the first rate; and altering the second focusing function at a rate that exceeds the first rate.

A method for changing focus may be provided. The method may include receiving a first light beam through an input facet of a core made of ultraviolet durable material, wherein refractive indices of the core are responsive to an electric field applied on the core; inducing, by a first set of electrodes that is connected to a first facet of the core that differs from the input facet, an electrical field having a magnitude that has a substantially parabolic shape along a first direction thereby causing the core to apply a first focusing function along the first direction on the first light beam, wherein the first direction is oriented to a propagation direction of the first light beam; and performing a fast change in the electrical field induced by the first set of electrodes thereby performing fast changes in the first focusing function.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

FIG. 16 is a flow chart illustrating a method according to an embodiment of the invention.

DETAILED DESCRIPTION

Figure 1:
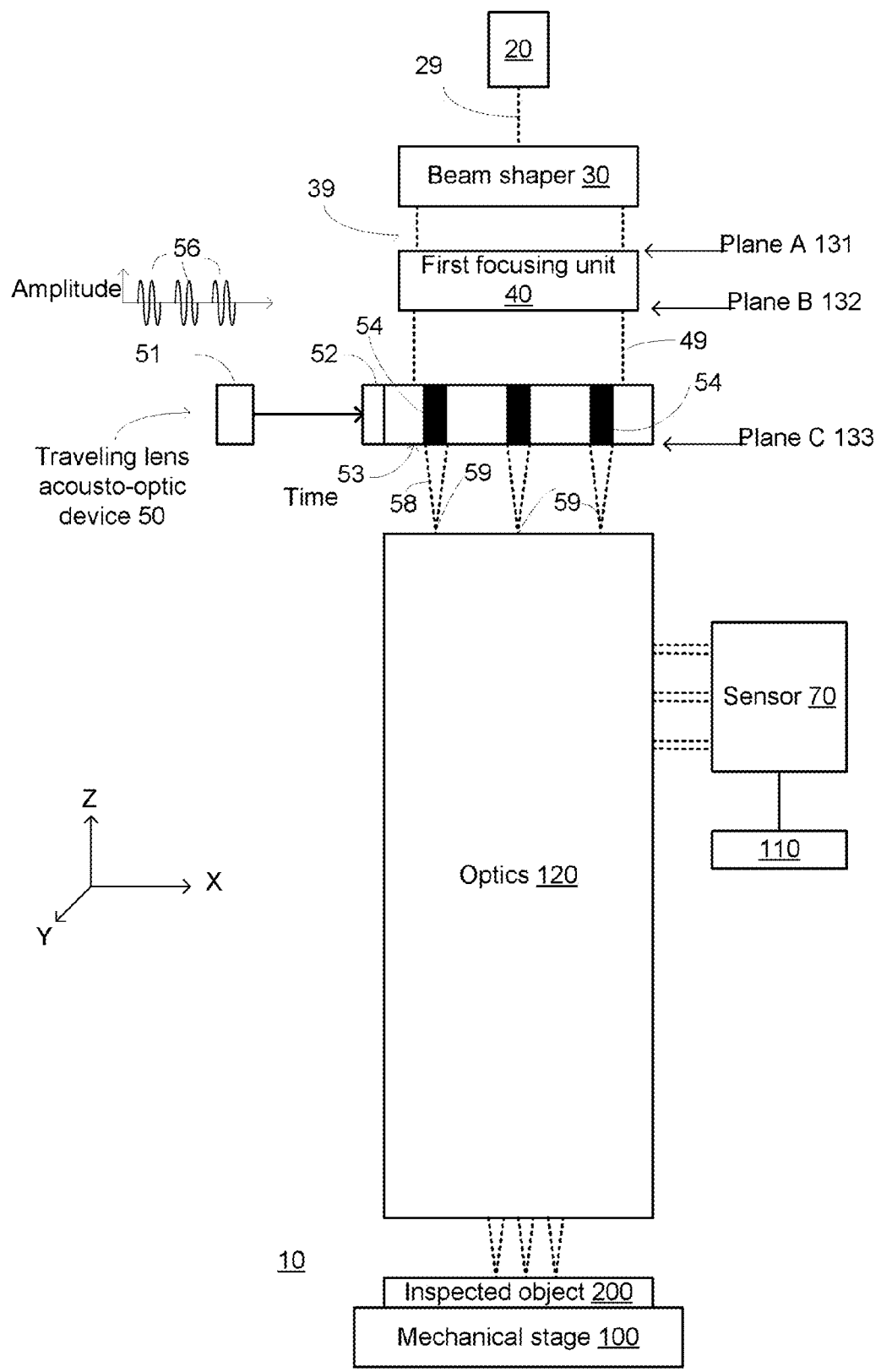
FIG. 1 illustrates an inspection system according to an embodiment of the invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The following detailed description is of exemplary embodiments of the invention but the invention is not limited thereto, as modifications and supplemental structures may be added, as would be apparent to those skilled in the art. In particular, but without limitation, while an exemplary embodiment may be disclosed with regard to the inspection of a inspected object surface by detecting reflected light using a light source and detecting unit that are disposed on a common side of a inspected object (a "reflective system"), it would be readily apparent to one skilled in the art that the teachings are readily adaptable to the inspection of a inspected object by detecting transmitted light with a detecting unit that is on a side of a inspected object opposite to that of the light source (a "transmissive system"). While the reflective system and the transmissive system differ, for example by the absence of a beam splitter in the transmissive system, the principles of the present invention are applicable to both types of systems. As would be understood by one skilled in the art, both types of systems may be utilized separately or together in the inspection of an inspected object, in accordance with the present invention.

In the following example a set of coordinates and directions is defined. These definitions are provided for simplicity of explanation only. The directions are referred to being mutually perpendicular to each other and parallel to the X, Y and Z axes. This is not necessarily so. In the examples set forth in FIGS. 1-4 light propagates along the Z axis, traveling lenses travel along the X axis, focus error corrections are aimed to elevate or lower the focal plane, the first direction is parallel to the Y axis and the second and third directions are parallel to the X axis.

FIG. 1 illustrates an inspection system 10 and inspected object 200 according to an embodiment of the invention.

Without limitation and only by example, the inspected object 200 may be any semiconductor product, such as an eight inch or twelve inch wafer or the like having multiple semiconductor devices thereon, at any of several stages of manufacture, or may be a mask, reticule or the like used in a manufacturing process, where such inspected object can be inspected for defects, foreign objects or pattern accuracy. It is desirable in such systems to identify with high accuracy and reliability the size, location and type of structure, defect or object that appears on the inspected object surface. It also is desirable to undertake such identification at high speed, in order to minimize the delay in the manufacturing process that is provided to the inspection and quality assurance steps.

The system 10 may rely upon a bright light source, such as a continuous (or pulsed) laser 20 that produces an initial beam 29. The initial beam 29 is applied to a beam shaper 30 having a conventional design, which may expand and collimate the beam 29 to form a first beam 39 having a uniform intensity beam profile in a manner known in the art. For wafer inspection, the laser preferably operates at a short wavelength, for example, 248 nm or 193 nm, in order to produce high resolution, with stable output power (or stable pulse energy and pulse rate), a stable transverse mode and a stable beam pointing.

Figure 12:
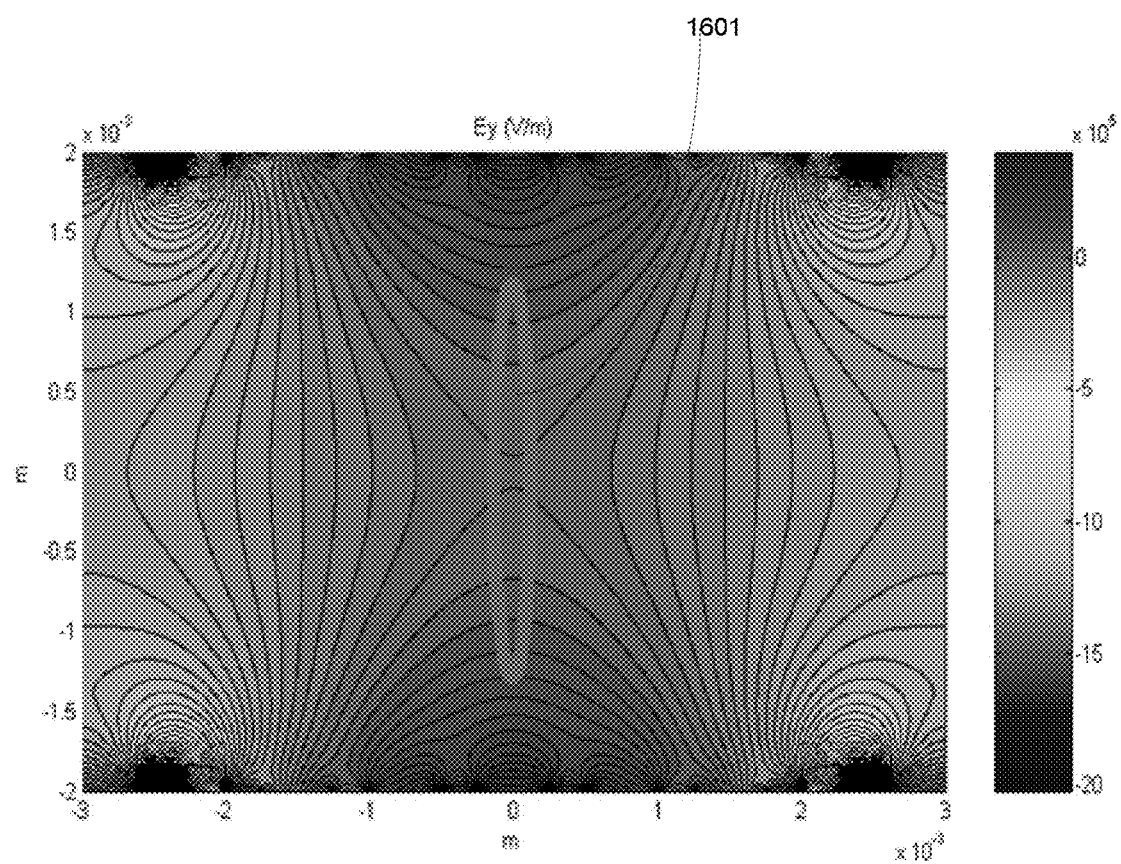
FIG. 12 illustrates a first beam that has an elliptic cross section and an electric field developed over a cross section of a core of a first focusing unit, according to an embodiment of the invention.

According to an embodiment of the invention the beam shaper 30 may shape the cross section of the first beam 39 by focusing, defocusing, filtering or using other well known techniques in order to provide a desired cross section. For example, the first beam 39 can have an elliptic shape, as illustrated in FIG. 12 in which the cross section 1601 of the first beam 39 has shape of a narrow ellipse—having its major axis along a first axis and its much smaller minor axis along a third axis.

The first beam 39 is provided to a first focusing unit 40. The first focusing unit 40 outputs a second beam 49.

The second beam 49 is projected onto a traveling lens acousto-optic device 50 that is operative to convert the second beam 49 into a plurality of beamlets 58. While three beamlets 58 are shown in FIG. 1 for convenience by way of example, the number of beamlets may be greater and in an exemplary embodiment may be ten or more concurrently scanning beamlets.

The traveling lens acousto-optic device 50 includes a radio frequency generator 51, a radio frequency input 52, and a crystal 53. The radio frequency (RF) generator 51 generates and sends to the RF input 52 chirped RF pulses 56, wherein a single RF pulse results in the generation of a single lens 54 and the series of pulses resulting in the formation of multiple cascaded lenses in the crystal 53 of the traveling lens acousto-optic device 50.

Each lens 54 will receive and focus the second beam 49 or a portion thereof at its output, thereby forming the desired number of beams. As the RF pulses 56 migrate through the crystal 53, the associated lenses will travel, causing each of their beams to move in the nature of a scan.

The basic theory, structure and materials of the acousto optic cell are taught in "Optical Scanning", edited by Gerald F. Marshall, Chapter 11 (published by Marcel Dekker, Inc. in 1991). As explained at pages 675-677, frequency chirp scanning of a single beam involves an acousto optic Bragg cell to which a linear frequency sweep (the "chirp") is applied. A frequency gradient produced across the optical aperture of the cell will act as a cylindrical lens whose focal length is based on the chirp rate. The light diffracted by the linearly swept acoustic frequency may be converging or diverging, and may be compensated by complementary optical lenses.

The crystal 53 can be made of a material that is compatible with a UV light source, preferably having an acousto-optic medium made of fused silica, GaAs or $TeO_2$ glass, although other known materials having UV light compatibility, may be used. The crystal 53 may have as an anti-reflective coating on each major side that is rated at less than 0.5% for both sides. The device will operate in a longitudinal acoustic mode at a wavelength of 266 nm and at a center frequency of 200 MHz with a bandwidth of 130 MHz. RF power may be less than 3.0 watts. The active aperture of the device may be 1.0 mm "H" by 60 mm "L" in one exemplary embodiment.

The RF generator 51 may provide a series of "chirps" or pulsed RF wave forms 56, which optimally are identical in duration and amplitude in an exemplary embodiment, but may differ in accordance with the desired optical effect of the traveling lens, to the RF input port 52. The RF input port 52 is positioned so as to be transverse to the path of light and enables the RF waveforms to be injected at the edge of the crystal 53 and to establish a pressure wave that traverses the length of the crystal 53 at a velocity that, in an exemplary embodiment, is 5.96 mm/micro-second or approximately the speed of sound. The pressure waves that propagate through the crystal medium are aligned to provide cascaded focusing lenses 54 for second light beam 49 that passes into an upper surface of the crystal 53 and exits from a lower surface of the crystal 53.

The effect of the creation of multiple cascaded lenses 54 in the crystal 53 (the active region of the acousto optic device 50) may result in the production of a beamlets 58 that have flying spots 59 at the focus plane of the traveling lens acousto optics device 50 for each of the created lenses. The flying spots 59 can be imaged onto the inspected object 200 by optics 120 to form multiple spots on the upper surface of the inspected object 200.

Light that is reflected from the inspected object 200 passes again through at least a portion of optics 120 and is directed towards sensor 70.

Sensor 70 generates detection signals in response to light that impinges upon it. These detection signals can be processed by processor 110.

The processor 110 can calculate or otherwise detect focus errors and control focusing characteristics of first focusing unit 40, traveling lens acousto-optic device 50 or both. Thus, the focal plane of the flying spots can be defined at a higher or lower point (as measured along an axis of propagation towards inspected object 200) and the focal plane of the first focusing unit 40 can also be defined at a higher or lower point.

In essence, if the focus error will be amended by elevating the focal point of the spots by a distance of J then each of the first focusing unit 40 and the traveling lens acousto-optic device 50 can be instructed to change its respective focal plane by K, wherein K is responsive to J and to the transfer function of optics 120 as the transfer function may "translate" a change of focal plane of K by these two components (40 and 50) to a focal plane change of J near the surface of the inspected object 200.

It is noted that the focus correction can use either one of a separate optical path, a separate sensor and a separate focus error calculator but such separate components were not shown for simplicity of explanation.

Figure 2:
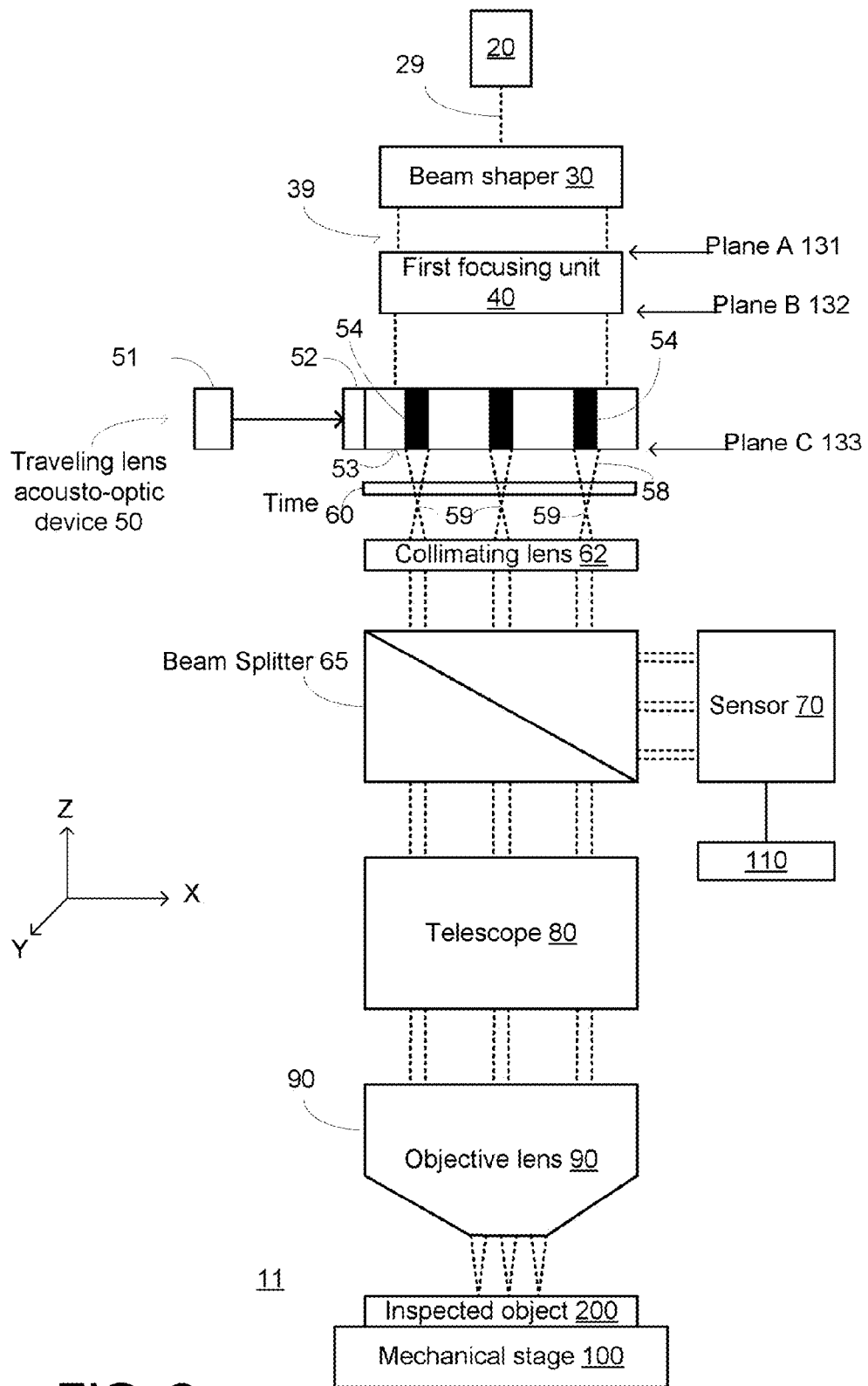
FIG. 2 illustrates an inspection system according to an embodiment of the invention.

FIG. 2 illustrates an inspection system 11 and inspected object 200 according to an embodiment of the invention.

The optics 120 of inspection system 10 are replaced by a collimating lens 62, a cylindrical lens 60, beam splitter 65, telescope 80 and objective lens 90 of inspection system 11.

The cylindrical lens 60 may perform a fixed focusing function along the first direction or along the second direction.

The cylindrical lens 60 may be followed by a collimating lens 62 that collimates the beamlets 58 to provide collimated beams. The collimated beams (one for each traveling lens) are sent to a beam splitter 65 that passes these beams towards telescope 80 and objective lens 90 to form a sequence of flying spots on the surface of the inspected object 200. Light from the inspected object 200 is directed through the objective lens 90 and the telescope 80 and impinges on the beam splitter 65 that directs the light towards the sensor 70.

Figure 3:
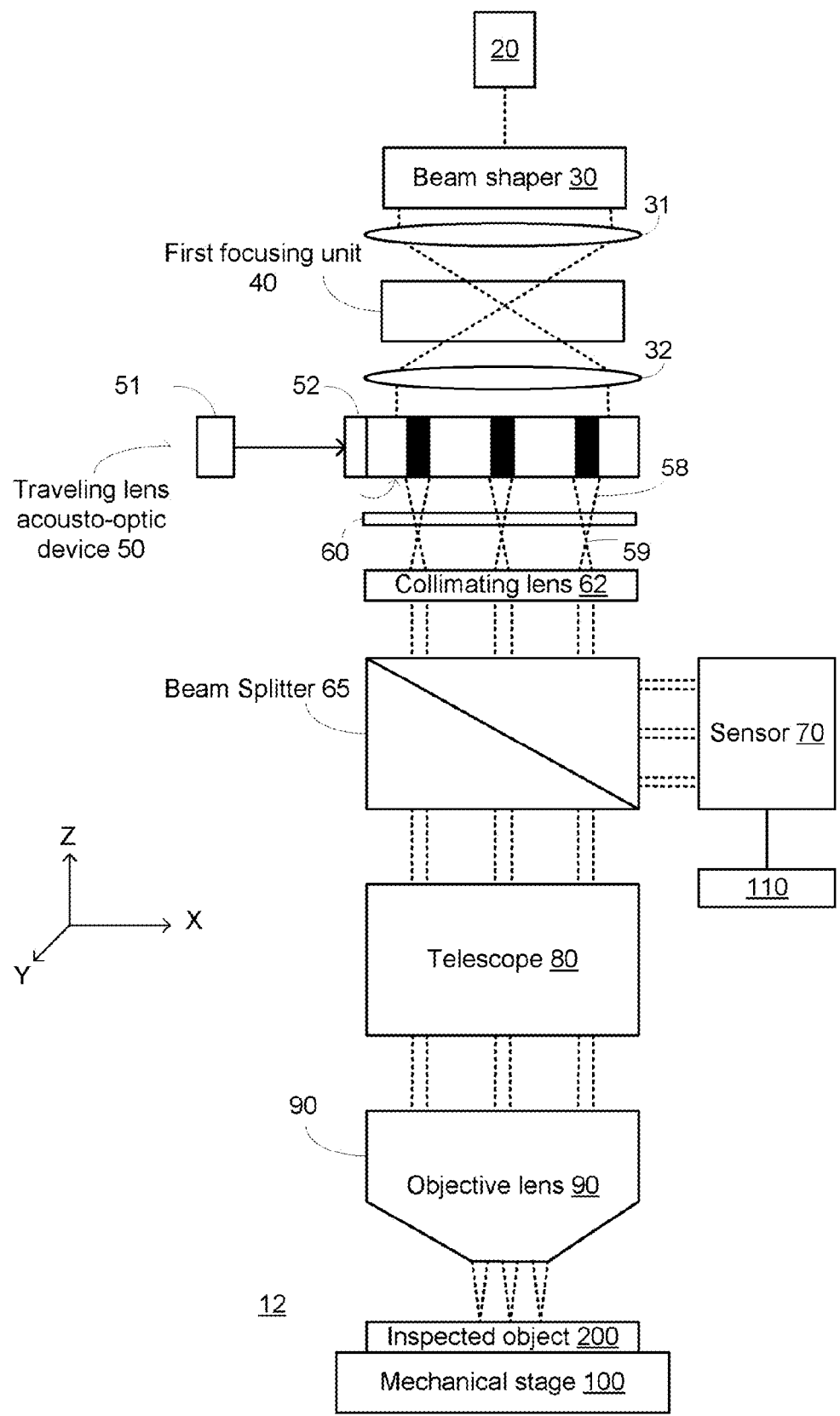
FIG. 3 illustrates an inspection system according to an embodiment of the invention.

FIG. 3 illustrates an inspection system 12 and inspected object 200 according to an embodiment of the invention.

Inspection system 12 differs from inspection system 11 by having: (a) a focusing lens 31 before the first focusing unit 40, the focusing lens 31 is aimed for focusing the input beam so that the first focusing unit 40 receives non-collimated light, and (b) a collimating lens 32, positioned after the first focusing unit 40, the collimating lens 32 is aimed to collimate the first light beam 39 before it reaches the traveling lens acousto-optic device 50.

The focusing lens 31 can focus the first beam 39 on an input facet 64 of the core of the first focusing unit or focus the first beam 39 on any other plane before or after plane A 131 in which the input facet 64 is located.

By focusing the first beam 39 or otherwise narrowing the width of the cross section of the first beam along the third direction an unwanted defocusing applied by the first focusing unit 40 (along the third direction) can be reduced. It is noted that the shaping of first beam 39 can be executed (at least partially) by beam shaper 30.

Figure 4:
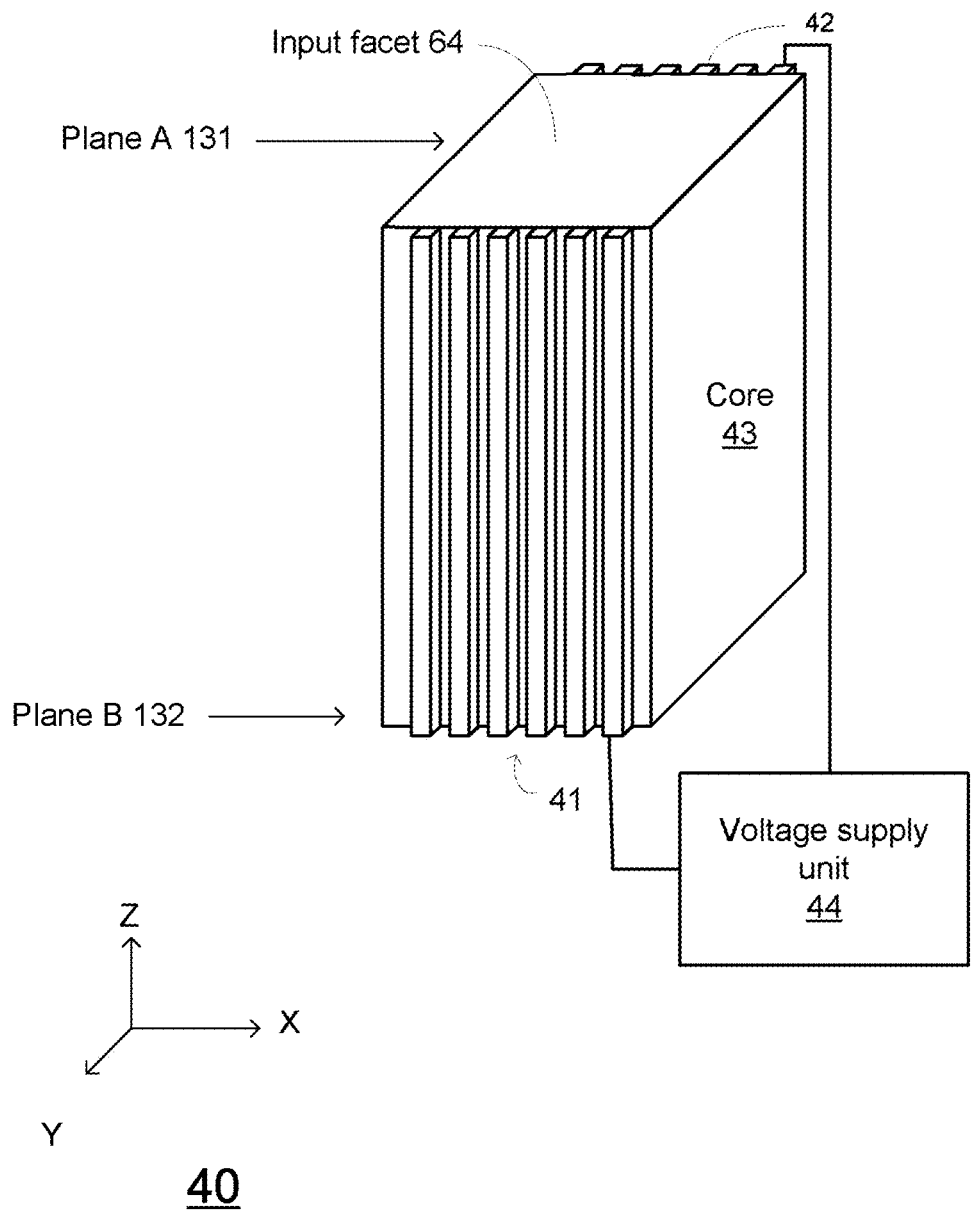
FIG. 4 illustrates a first focusing unit according to an embodiment of the invention.

FIG. 4 illustrates a first focusing unit 40 according to an embodiment of the invention. The first focusing unit 40 includes a core 43 that is connected to multiple electrodes. The electrodes can be arranged in one to more sets of electrodes.

The core 43 can be made of a crystal that lacks a center of symmetry—the atomic structure of the crystal does not have a center of symmetry. Refractive indexes of the core 43 can be responsive to an electric field applied on the core 43.

The core 43 should be made of durable ultra violate material (and especially durable deep ultra violet (DUV)) material that should also have good optical properties (allow a transmission of most radiation) and large EO coefficient. Non-limiting examples include Potassium Di-deuterium Phosphate (KD*P), $KH_2PO_4$ (KDP), Ammonium Dihydrogen Phosphate (ADP) and Silicone DiOxide (SiO2).

| Symmetry | $\epsilon/\epsilon_0$ | Index of refraction | $n_o^3 r \cdot 10^{-12}$ V/m | $EO \cdot 10^{-12}$ V/m | Material |
|---|---|---|---|---|---|
| 4̄2m | $\epsilon \parallel = 20$ | $n_0 = 1.51$ | 29 | $R_{41} = 8.6$ | KDP |
|  | $\epsilon \perp = 45$ | $n_e = 1.47$ | 34 | $R_{63} = 10.6$ |  |
| 4̄2m | $\epsilon \parallel c = 50$ | $n_0 = 1.49$ | 80 | $R_{41} = 8.8$ | KD*P |
|  | $\epsilon \perp c = 47$ | $n_e = 1.45$ |  | $R_{63} = 23.6$ |  |
| 4̄2m | $\epsilon \parallel c = 12$ | $n_0 = 1.52$ | 95 | $R_{41} = 28$ | ADP |
|  | $\epsilon \perp c = 55$ | $n_e = 1.48$ | 27 | $R_{63} = 8.5$ |  |
| 32 | $\epsilon \parallel c = 4.3$ | $n_0 = 1.54$ | 0.7 | $R_{41} = 0.2$ | SiO2 |
|  | $\epsilon \perp c = 3.3$ | $n_e = 1.55$ | 3.4 | $R_{63} = 0.93$ |  |

A core 43 was made of KD*P. Since KD*P is water soluble the electrodes should be deposited in a water free process thus chemical processes could not be used. The core 43 can be vaporized by a uniform gold layer on the top and bottom facets 46 and 45. Then, a focused infra red laser beam can be used to scribe the gold, burning lines across the surface of the core 43. The waste generated during the scribing process can be collected by air pressure.

In order to protect the interface the electrodes and protect the core 43 from making contact with air humidity, each electrode can be connected to a golden tip which is soldered to a terminal wire. The terminal wires are connected to a voltage supply source 44. It is noted that other alternative solutions can be applied.

FIG. 4 illustrates a first set of electrodes 41 and second set of electrodes 42. These two sets of electrodes receive voltage from voltage supply unit 44. Each electrode can receive different voltage levels and can cause the core 43 to apply one or more focusing functions.

Figure 5:
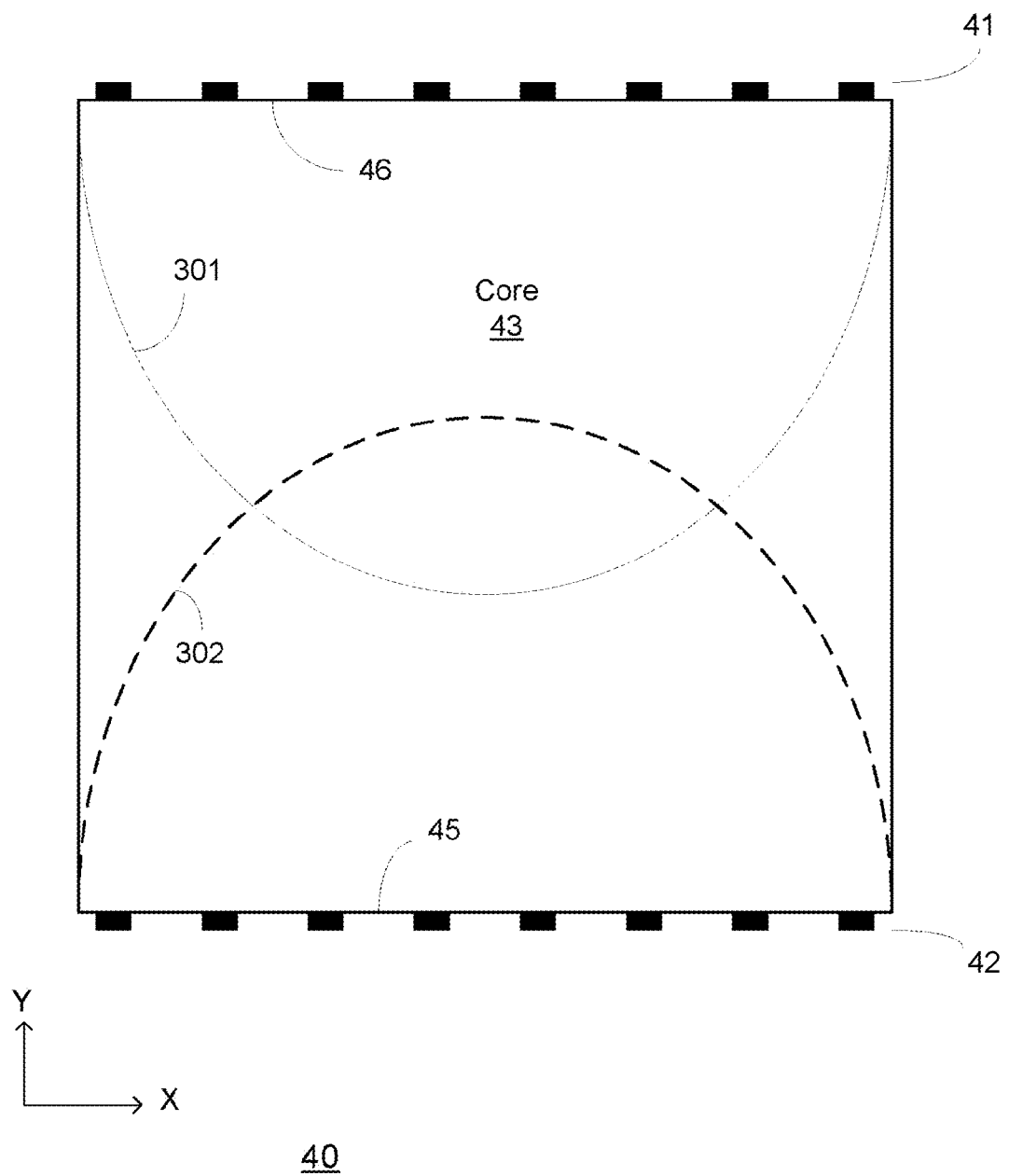
FIG. 5 illustrates electric fields developed over a cross section of a core of a first focusing unit, according to an embodiment of the invention.
Figure 6:
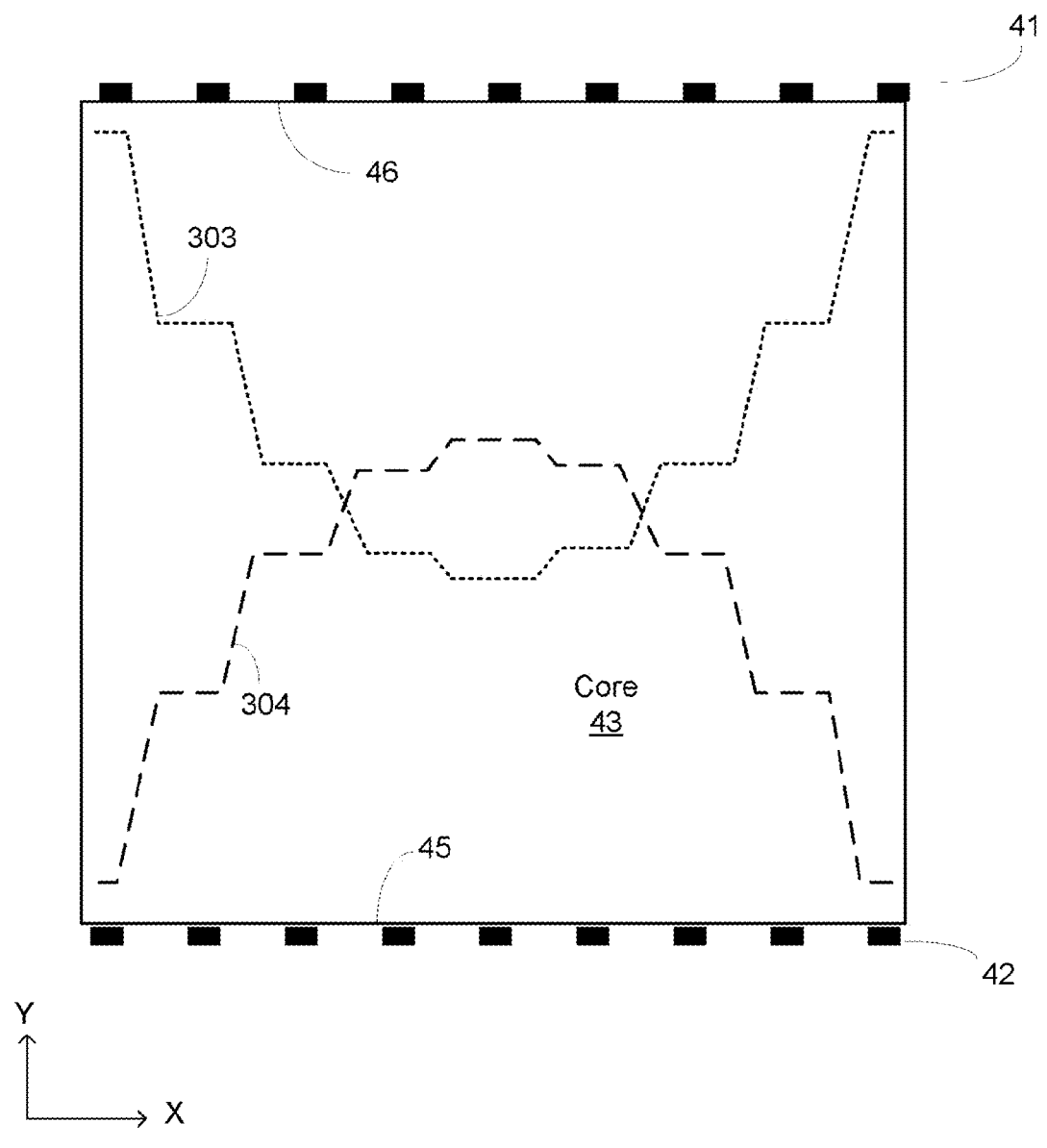
FIG. 6 illustrates an electric field developed over a cross section of a core of a first focusing unit, according to an embodiment of the invention.

FIG. 4 illustrates two sets of electrodes 41 and 42 that are connected to two opposite facets (denoted 46 and 45 in FIGS. 5 and 6). It is noted that the electrodes can be connected to more than two facets of the core, and that the core 43 can be shaped in different manners. For example, the core 43 can be shaped according to equi-potential shapes such as those illustrated in FIG. 16.

FIG. 4 illustrates electrodes that are parallel to each other, wherein each electrode can extend along the Z-axis. It is noted that the electrodes can be positioned in different manners and have different shapes. For example, the electrodes can be formed as a matrix or otherwise formed to allow the provision of different voltage values along the Z-axis.

It is further noted that the number of electrodes per set can differ from nine (as illustrated in FIGS. 5 and 6) or six (as illustrated in FIG. 4).

The core 43 can also apply a third focusing function along a third direction that is substantially normal to the first direction. This is illustrated, for example, in FIG. 15. When the first focusing function focuses the first beam along the first direction the third focusing function defocuses the first beam along the third direction.

According to an embodiment of the invention one set of electrodes 42 is arranged to induce an electrical field having a magnitude, along the first direction, that increases with a proximity to a center of the core. A second set of electrodes 41 can be arranged to induce an electrical field having a magnitude, along the first direction, that decreases with the proximity to the center of the core.

The electrodes are arranged to induce an electrical field that causes the core 43 to act as a positive lens along the first direction and to act as a negative lens along the third direction. These electrodes can be provided with different voltages that can cause the core 43 to act as a negative lens along the first direction and to act as a positive lens along the third direction.

FIG. 5 illustrates electric fields developed over a cross section of a core of a first focusing unit, according to an embodiment of the invention. The cross section is taken along an X-Y plane located between planes A 131 and B 132.

Curve 302 illustrates an electrical field having a magnitude that has a substantially inverted parabolic shape along the first direction and was induced by set of electrodes 42.

Curve 301 illustrates an electrical field having a magnitude that has a substantially parabolic shape along the first direction and was induced by set of electrodes 41.

FIG. 6 illustrates an electric field developed over a cross section of a core of a first focusing unit, according to an embodiment of the invention.

The parabolic shaped electric field can be roughly approximated in practice by a finite number of discrete steps. It is expected that this rough approximation will be smoothed toward the center of the core 43 so that the electric field will not have any discontinuities, and so it will change gradually and smoothly in the vicinity of the center. Discontinuities can only occur where there is an infinite charge density and in our model there is no (macroscopic) charge inside the crystal. On the other hand, close to the electrodes there will be sudden "jumps" in the magnitude of the electric field, as can be seen from the simulations.

Curve 304 illustrates an electrical field having a magnitude that is a rough approximation of an inverted parabolic shape along the first direction induced by set of electrodes 42.

Curve 303 illustrates an electrical field having a magnitude that is a rough approximation of a parabolic shape along the first direction induced by set of electrodes 41.

Figure 7:
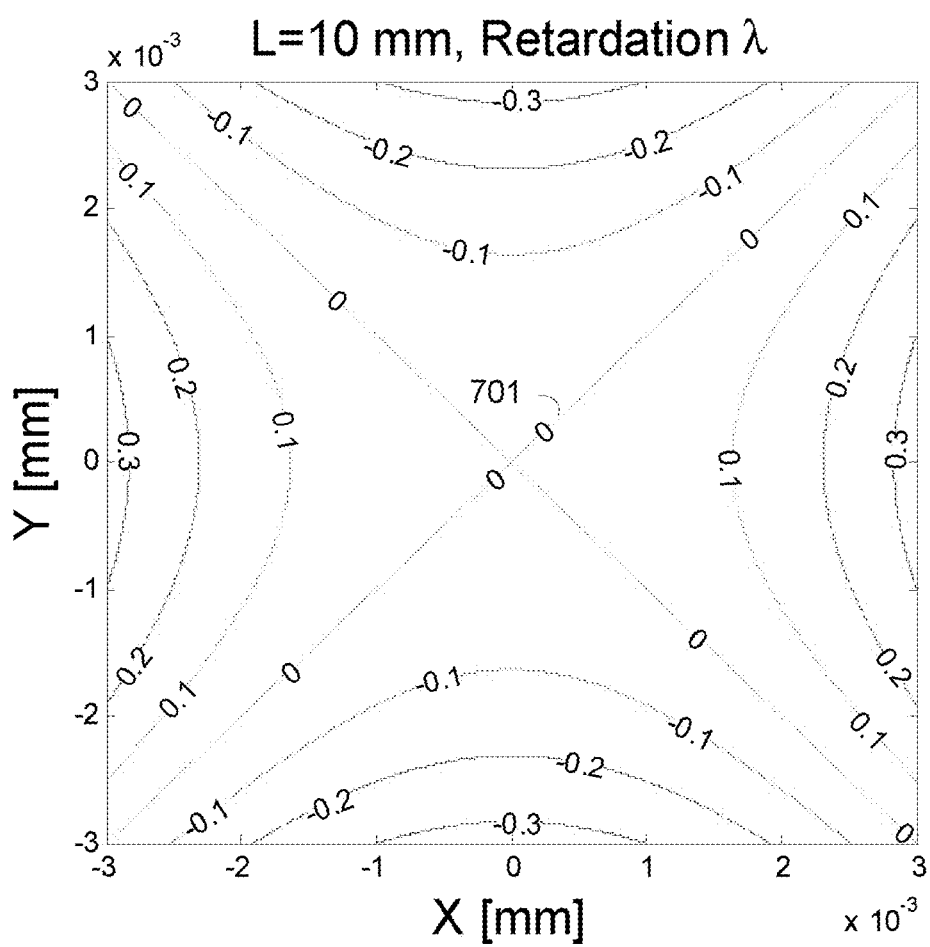
FIG. 7 illustrates a retardation developed over a core of a first focusing unit, according to an embodiment of the invention.

FIG. 7 illustrates a phase delay (retardation) resulting from the passage of light through the crystal (core) as a function of position which is calculated from an ideal Ey component of the electrical field by taking into account a length of the crystal and the refractive index of the crystal.

Figure 8:
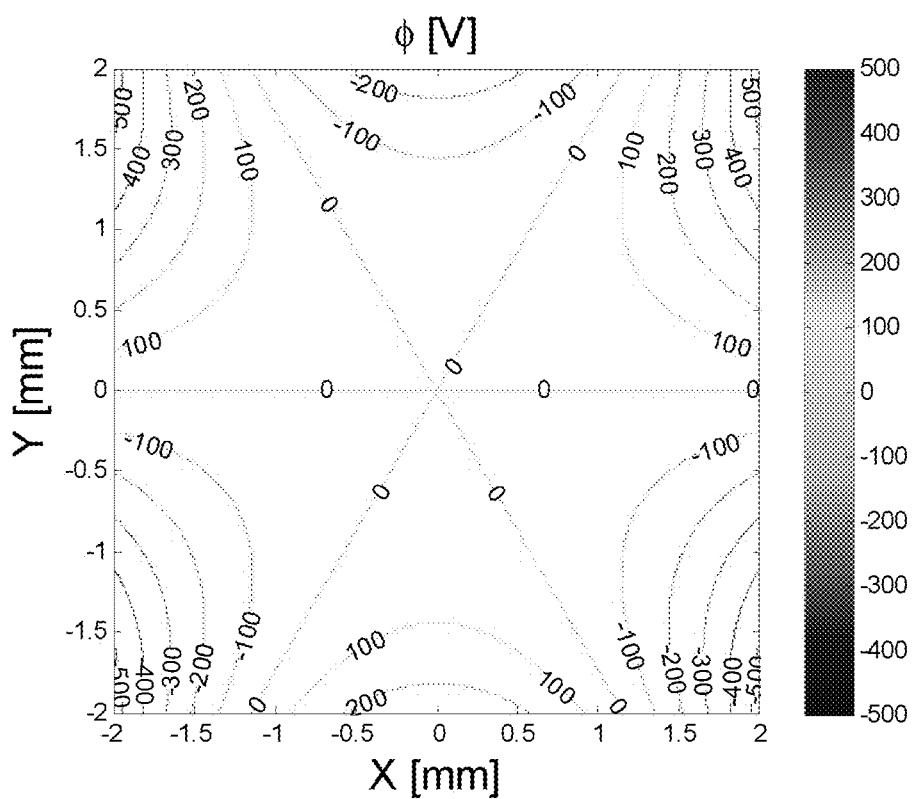
FIG. 8 illustrates an electric field developed over a cross section of a core of a first focusing unit, according to an embodiment of the invention.

FIG. 8 illustrates equi-potential lines along an X-Y plane within the core.

Figure 9:
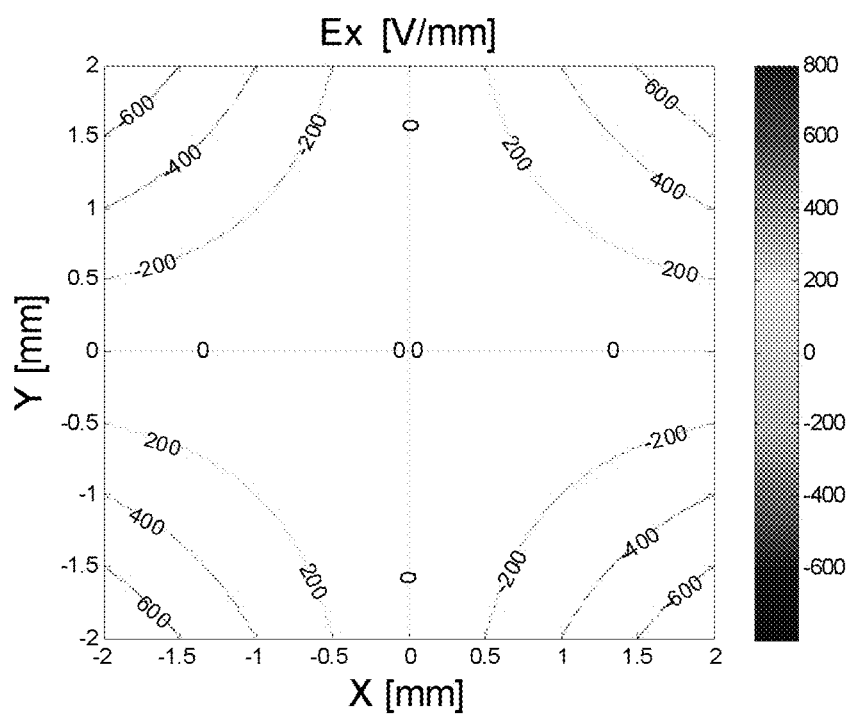
FIG. 9 illustrates an electric field developed over a cross section of a core of a first focusing unit, according to an embodiment of the invention.
Figure 10:
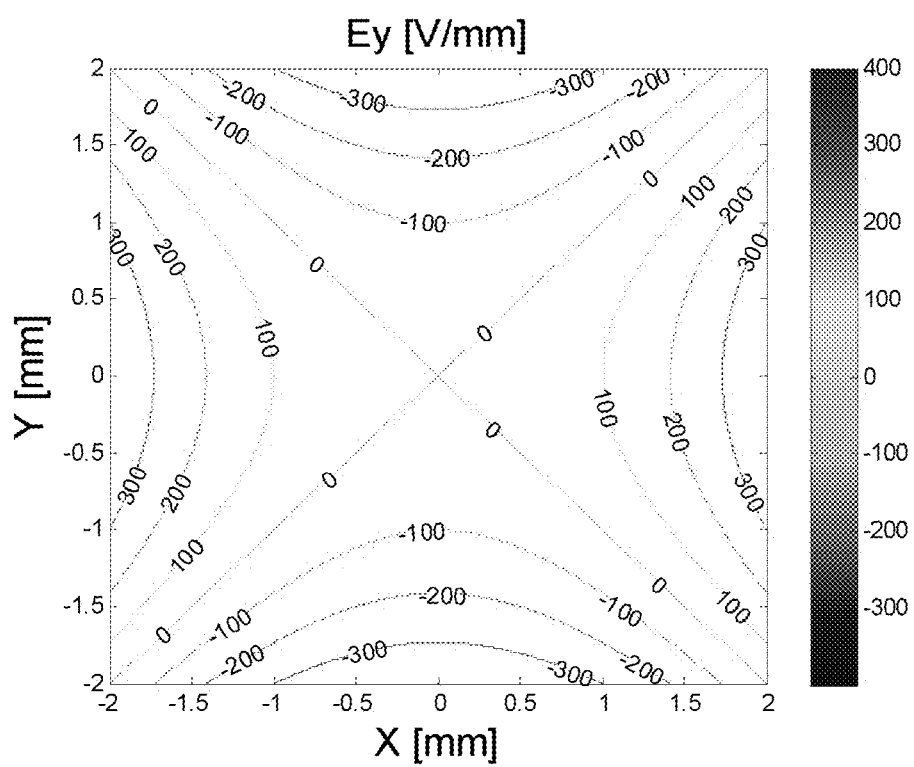
FIG. 10 illustrates an electric field developed over a cross section of a core of a first focusing unit, according to an embodiment of the invention.

FIG. 9 illustrates an Ex component of the electrical field while FIG. 10 illustrates the Ey component of the field.

Figure 11:
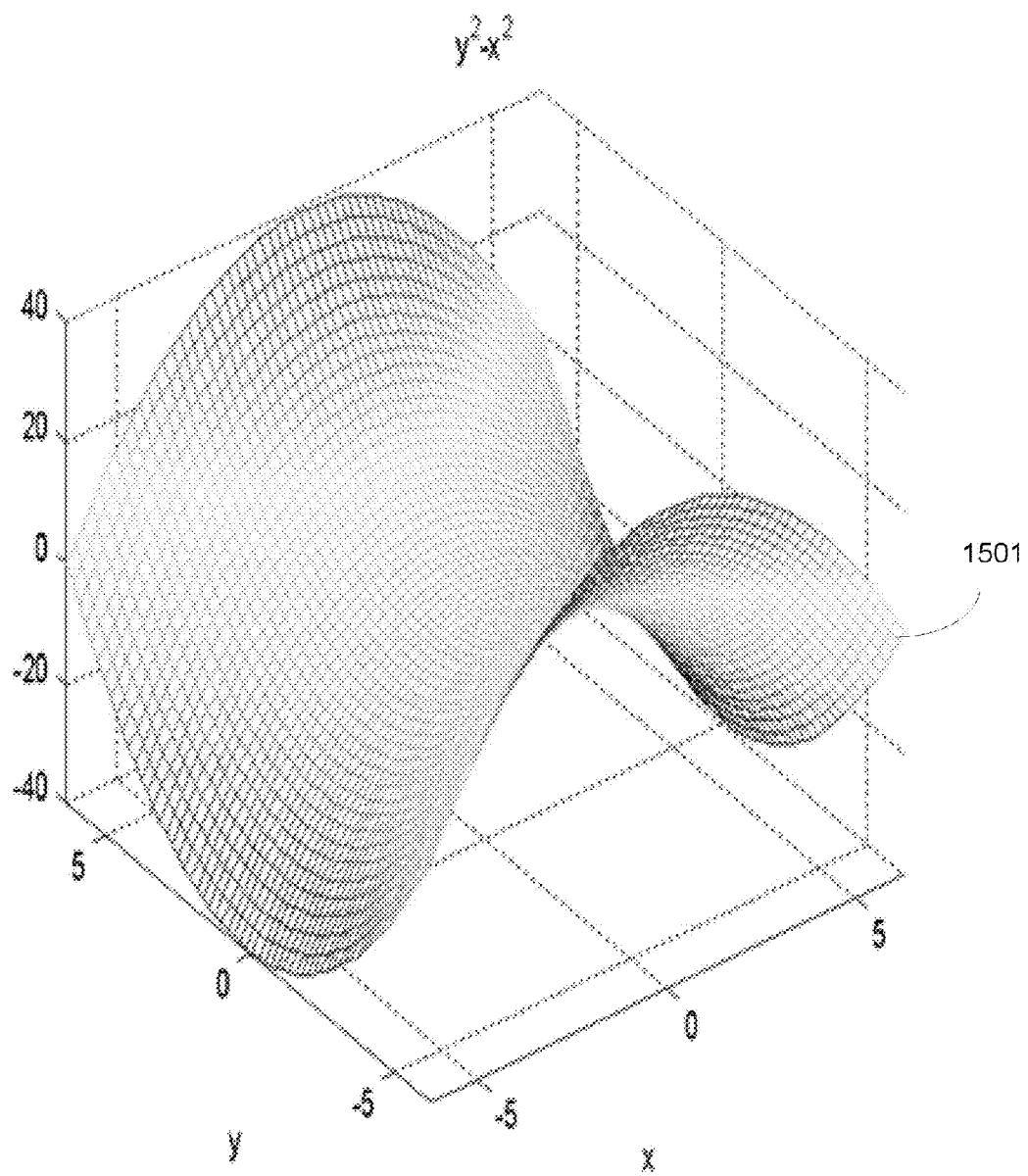
FIG. 11 illustrates the wave front of a second beam that exits the first focusing unit, according to an embodiment of the invention.

FIG. 11 illustrates the wave front of a second beam 49 that exits the first focusing unit 40, according to an embodiment of the invention. The wave front 1501 has a parabolic shape along the first direction and an inverted parabolic shape (saddle) along a third direction.

Figure 13:
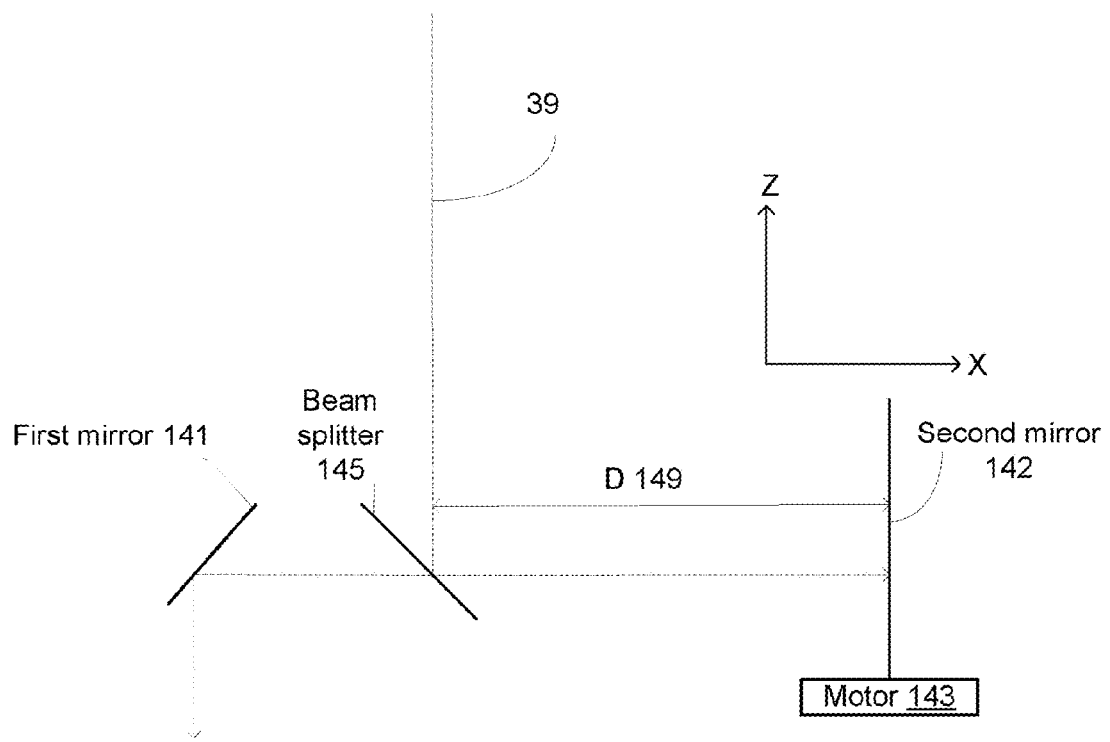
FIG. 13 illustrates a first focusing unit according to another embodiment of the invention.

FIG. 13 illustrates a first focusing unit 40 according to another embodiment of the invention.

The first focusing unit 40 changes the focal plane by changing a length of an optical path of the first beam 39 that propagates through the first focusing unit 40.

A second mirror is 142 movable (by a motor 143) along the X axis so as to change the distance D 149 between a beam splitter 145 and the second mirror 142 and thus changing the length of the optical path. The second mirror 142 is small and lightweight and can be moved relatively quickly.

The first beam 39 enters the first focusing unit 40 in parallel to the Z-axis. It is reflected by the beam splitter 145 towards the second mirror 142. The second mirror 142 reflects the light that passes through the beam splitter 145 until it impinges on first mirror 141. The first mirror 141 reflects the beam to provide a vertically propagating second beam 49.

Figure 14:
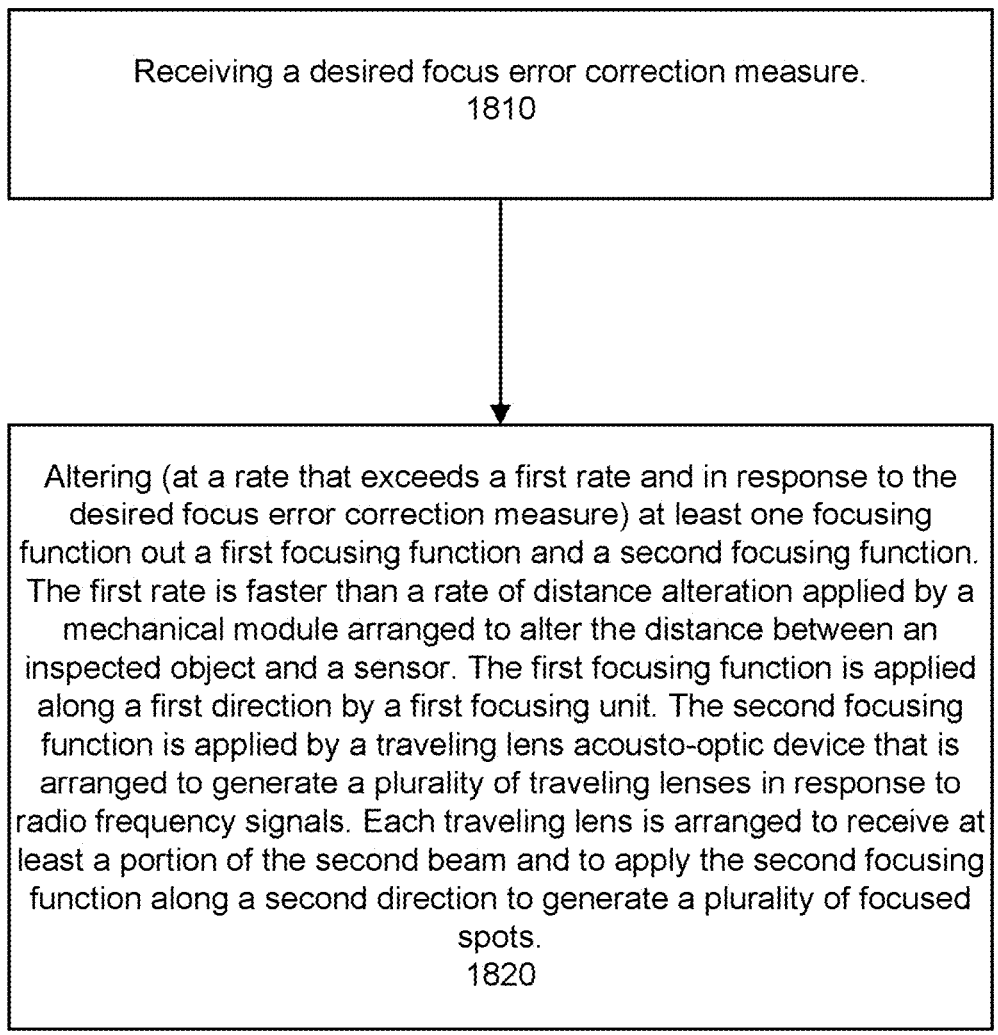
FIG. 14 is a flow chart illustrating a method according to an embodiment of the invention.

FIG. 14 illustrates a method 1800 according to an embodiment of the invention.

Method 1800 starts with step 1810 of receiving a desired focus error correction measure. The desired focus error correction measure can be computed by any conventional means.

Step 1810 is followed by step 1820 of altering (at a rate that exceeds a first rate and in response to the desired focus error correction measure) at least one focusing function out a first focusing function and a second focusing function.

The first rate is faster than a rate of distance alteration applied by a mechanical module arranged to alter the distance between an inspected object and a sensor.

The first focusing function is applied along a first direction by a first focusing unit.

The second focusing function is applied by a traveling lens acousto-optic device that is arranged to generate a plurality of traveling lenses in response to radio frequency signals. Each traveling lens is arranged to receive at least a portion of the second beam and to apply the second focusing function along a second direction to generate a plurality of focused spots.

Figure 15:
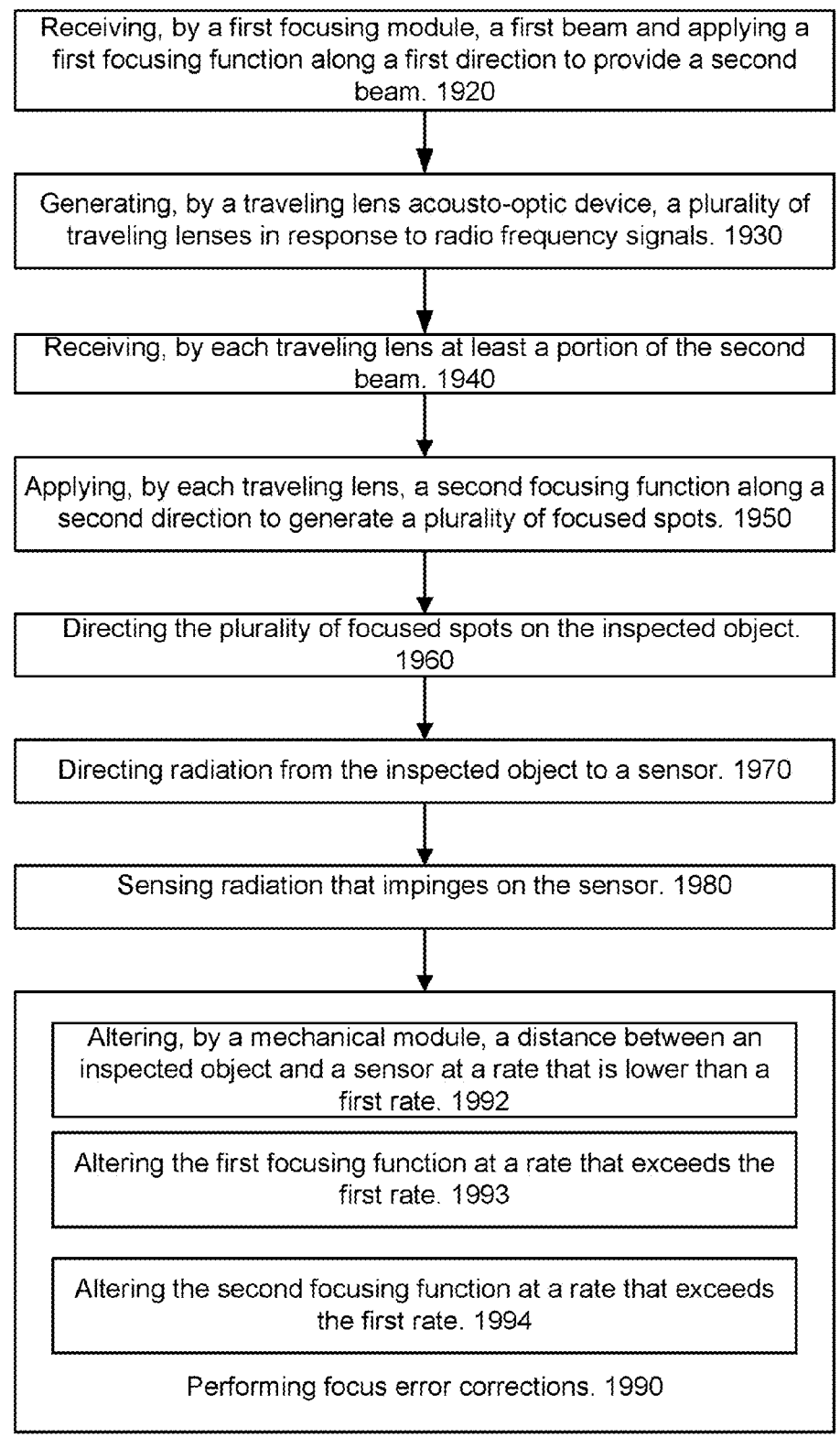
FIG. 15 is a flow chart illustrating a method according to an embodiment of the invention.

FIG. 15 illustrates a method 1900 according to an embodiment of the invention.

Method 1900 starts with step 1920 of receiving, by a first focusing module, a first beam and applying a first focusing function along a first direction to provide a second beam.

Step 1920 is followed by step 1930 of generating, by a traveling lens acousto-optic device, a plurality of traveling lenses in response to radio frequency signals.

Step 1930 is followed by step 1940 of receiving, by each traveling lens at least a portion of the second beam.

Step 1940 is followed by step 1950 of applying, by each traveling lens, a second focusing function along a second direction to generate a plurality of focused spots.

Step 1950 is followed by step 1960 of directing the plurality of focused spots on the inspected object.

Step 1960 is followed by step 1970 of directing radiation from the inspected object to a sensor.

Step 1970 is followed by step 1980 of sensing radiation that impinges on the sensor.

During the execution of steps 1920-1980, method 1900 also performs focus error correction, as illustrated by step 1990 of performing focus error corrections.

Step 1990 may include any one of steps 1992, 1993 and 1994.

Step 1992 includes altering, by a mechanical module, a distance between an inspected object and a sensor at a rate that is lower than a first rate.

Step 1993 includes altering the first focusing function at a rate that exceeds the first rate.

Step 1994 includes altering the second focusing function at a rate that exceeds the first rate.

FIG. 16 illustrates a method 2000 according to an embodiment of the invention.

Method 2000 starts by steps 2010 and 2020.

Step 2010 includes receiving a first light beam through an input facet of a core made of ultraviolet durable material; wherein refractive indices of the core are responsive to an electric field applied on the core.

Step 2020 includes inducing, by a first set of electrodes that is connected to a first facet of the core that differs from the input facet, an electrical field having a magnitude that has a substantially parabolic shape along a first direction thereby causing the core to apply a first focusing function along the first direction on the first light beam; wherein the first direction is oriented to a propagation direction of the first light beam.

Steps 2010 and 2020 can be repeated multiple times.

In parallel to the execution of these steps, method 2000 may also include performing a focus error correction process, as illustrated by step 2030 of performing a fast change in the electrical field induced by the first set of electrodes thereby performing fast changes in the first focusing function. The change is fast as it is faster (and even much faster) than a change of focus that required moving (elevating or lowering) the inspected object, the optics and the like.

Figure 17:
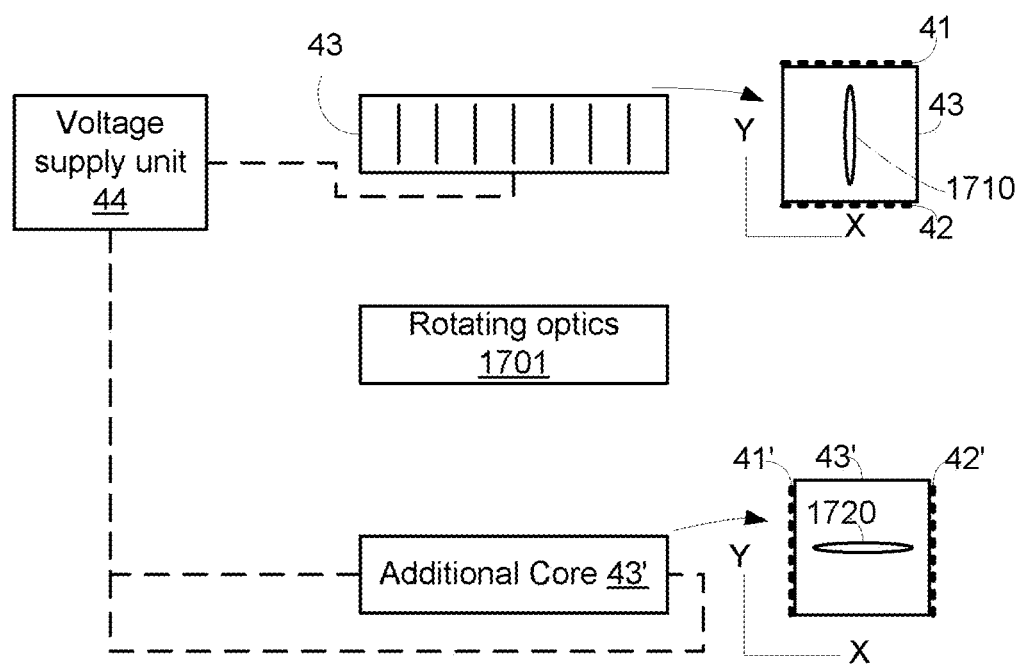
FIG. 17 illustrates a first focusing unit according to an embodiment of the invention.

FIG. 17 illustrates a first focusing unit 40 according to another embodiment of the invention.

The first focusing unit 40 includes a core 43, rotating optics 1701 and an additional core 43'. Core 43 is rotated (about the Z-axis) by about ninety degrees to core 43. If, for example the sets of electrodes 41 and 42 are parallel to the plane of the page including FIG. 17, the sets of electrodes 41' and 42' of the additional core 43' are perpendicular to the plane of the page including FIG. 17.

The first beam—when it impinges on core 43—has a cross section 1710 that has a narrow elliptic shape—having its major axis parallel to the Y axis, thus minimizing the unwanted focusing or defocusing effect along a third direction.

The beam that is output from core 43 is rotated by about ninety degrees by rotating optics 1701 (that may include any known rotating optics such as a set of prisms) so that when it impinges on the additional core 43' the cross section 1720 has a narrow elliptic shape—having its major axis parallel to the X axis.

This configuration allows controlling the focusing along the first and third directions and can be applied in addition to or instead of the altering focusing function applied by the traveling lens acousto-optic device 50.

Calculations, Theory

The following calculations provide an example of electric fields applied on an electro optic lens such as core 43—a lens whose power can be controlled by electric potential. The induced lens is of the graded index type. It has a parabolic refraction index and acts as focusing lens, so by taking a material with a non-zero electro optics coefficient and inducing a an electric field into it, whose amplitude changes as function $x^2$, a lens will be formed. By using the electro optics (EO) tensor the new indices ellipsoid can be calculated and lens performance evaluated and optimized.

Electric Field Calculations

In order to get a parabolic refraction index the electric field should be of the form $E_y \propto \alpha x^2$ Or in a more general form:

$$E_y = \alpha x^2 f(y) + g(y)$$

The electric field must obey the Maxwell's equation:

$$\vec{\nabla} \cdot \vec{E} = 0; \Rightarrow \frac{\partial E_x}{\partial x} + \frac{\partial E_y}{\partial y} = 0$$

$$\vec{\nabla} \times \vec{E} = 0; \Rightarrow \frac{\partial E_y}{\partial x} - \frac{\partial E_x}{\partial y} = 0$$

These two equations provide:

$$\frac{\partial E_x}{\partial x} + \alpha x^2 f'(y) + g'(y) = 0$$

$$2\alpha x f(y) - \frac{\partial E_x}{\partial y} = 0$$

These equations can be integrated to obtain:

$$E_x = -\frac{\alpha x^3}{3} f'(y) - g'(y)x + c(y)$$

-continued $$\Rightarrow 2\alpha x f(y) + \frac{\alpha x^3}{3} f''(y) + g''(y)x + c'(y) = 0$$

Since $E_y$ should be quadratic in the x-direction, this imposes the following restrictions:

$$f''(y)=0; \Rightarrow f(y)=a_1 y+b_1$$

$$2\alpha f(y)-g''(y)=0$$

$$c'(y)=0 \Rightarrow c(y)=const=c$$

Solving for g(y):

$$g(y) = -2\alpha\left(a_1 \frac{y^3}{6} + b_1 \frac{y^2}{2} + c_1 y + d_1\right)$$

Since g and f were obtained, the fields can be calculated:

$$E_x = -\alpha \frac{x^3}{3} a_1 - 2\alpha x\left(a_1 \frac{y^2}{2} + b_1 y + c_1\right) + c$$

$$E_y = \alpha x^2(a_1 y + b_1) - 2\alpha\left(a_1 \frac{y^3}{6} + b_1 \frac{y^2}{2} + c_1 y + d_1\right)$$

From these equations the potential can be calculated:

$$\vec{E} = -\nabla \phi;$$

$$E_x = -\frac{\partial \phi}{\partial x}; E_y = -\frac{\partial \phi}{\partial y}$$

And by direct integration:

$$\phi(x, y) =$$
$$-\alpha \frac{x^4}{12} a_1 + \alpha x^2\left(a_1 \frac{y^2}{2} + b_1 y + c_1\right) + cx - 2\alpha\left(a_1 \frac{y^4}{24} + b_1 \frac{y^3}{6} + c_1 \frac{y^2}{2} + d_1 y\right)$$

From practical point of view it is desirable to have: $\phi(x, y) = -\phi(x, -y)$.

This shall allow using symmetric supply voltages.

This condition implies $a_1=0$. C and $d_1$ will contribute only a constant field, so the final result is:

$$\phi(x, y) = b_1 x^2 y - b_1 \frac{y^3}{3};$$

$$-E_y = \frac{\partial \phi}{\partial y} = b_1(x^2 - y^2);$$

$$-E_x = \frac{\partial \phi}{\partial x} = 2b_1 x \cdot y;$$

It can be seen that $E_y$ behaves as was desired, but $E_x$ differs from this desired goal so that care should be taken for this field component when coupling to the crystal an EO tensor.

It can be seen that the $E_y$ field has the shape of a saddle point (inverted parabolic shape) so in one direction a positive lens is provided and in the orthogonal direction a negative lens is provided.

Potassium Di-deuterium Phosphate has an index ellipsoid equation of:

$$: \frac{x^2}{n_o^2} + \frac{y^2}{n_o^2} + \frac{z^2}{n_e^2} + 2r_{41}E_x yz + 2r_{41}E_y xz + 2r_{63}E_z xy = 1$$

The coordinate system is the crystal system. In order to remove confusion, the crystal coordinate system will be denoted as $(x,y,z) \Rightarrow (s,v,t)$ where t is the c direction of the crystal (direction with different refraction index).

In order to get the EO lens, $E_y$ will be applied in the t direction. The index ellipsoid equation will be:

$$\frac{s^2}{n_o^2} + \frac{v^2}{n_o^2} + \frac{t^2}{n_e^2} + 2r_{63}E_y sv = 1$$

By coordinate transformation this equation can be diagonalized.

$$s=s' \cos 45° - v' \sin 45°$$

Define:

$$v=s' \sin 45° + v' \cos 45°$$

And the index ellipsoid equation is:

$$\left(\frac{1}{n_o^2} + r_{63}E_y\right)s'^2 + \left(\frac{1}{n_o^2} - r_{63}E_y\right)v'^2 + \frac{t^2}{n_e^2} = 1$$

The effect of the electric filed was to change the refraction index and a new optical direction was created at 45° to the crystal direction. The change in refraction index can be calculated:

$$n_{s'} = n_o - \frac{n_o^3}{2} r_{63} E_y$$

$$n_{v'} = n_o + \frac{n_o^3}{2} r_{63} E_y$$

If light is propagated in the 110 direction of the crystal and polarization in the 110 direction, the refraction index will be $n_s'$.

Since in the field equations $E_x$ could not be eliminated, its effect on the refraction index should be considered. The index ellipsoid with Ex is:

$$\text{is}: \left(\frac{1}{n_o^2} + r_{63}E_y\right)s'^2 + \left(\frac{1}{n_o^2} - r_{63}E_y\right)v'^2 + \frac{t^2}{n_e^2} + 2r_{41}E_x\left(\frac{s'}{\sqrt{2}} + \frac{v'}{\sqrt{2}}\right)t = 1$$

After some algebra:

$$\frac{s'^2}{n_{o1}^2} + \frac{v'^2}{n_{o2}^2} + \frac{t^2}{n_e^2} + \sqrt{2} r_{41} E_x s' t + \sqrt{2} r_{41} E v' t = 1$$

To find the new major direction of the index ellipsoid the eignvalues and eigen vectors of the quadratics form matrix should be found:

$$\Delta = \begin{bmatrix} \frac{1}{n_{o1}^2} & 0 & \frac{r_{41}}{\sqrt{2}} E_x \\ 0 & \frac{1}{n_{o2}^2} & \frac{r_{41}}{\sqrt{2}} E_x \\ \frac{r_{41}}{\sqrt{2}} E_x & \frac{r_{41}}{\sqrt{2}} E_x & \frac{1}{n_e^2} \end{bmatrix}$$

The determinant is:

$$\Delta = \left(\frac{1}{n_{o1}^2} - \lambda\right) \cdot \left(\frac{1}{n_{o2}^2} - \lambda\right) \cdot \left(\frac{1}{n_e^2} - \lambda\right) - \frac{r_{41}^2}{2} E_x^2 \cdot \left(\frac{1}{n_{o1}^2} + \frac{1}{n_{o1}^2} - 2\lambda\right)$$

Since $$\frac{r_{41}^2}{2} E_x^2$$

is very small it can be treated as perturbation to the roots $$\left(\frac{1}{n_{o1}^2}; \frac{1}{n_{o2}^2}; \frac{1}{n_e^2}\right),$$

using the Newton-Raphson method to find the correction to the roots, i.e.:

$$\lambda_{i+1} = \lambda_i - \frac{\Delta(\lambda_i)}{\Delta'(\lambda_i)}$$

Thus, the correction to the roots is obtained:

$$\delta\left(\frac{1}{n_{o1}^2}\right) = \frac{\frac{r_{41}^2}{2} E_x^2 \left(\frac{1}{n_{o2}^2} - \frac{1}{n_{o1}^2}\right)}{\frac{r_{41}^2}{2} E_x^2 - \left(\frac{1}{n_{o2}^2} - \frac{1}{n_{o1}^2}\right)\left(\frac{1}{n_e^2} - \frac{1}{n_{o1}^2}\right)} \cong \frac{\frac{r_{41}^2}{2} E_x^2}{\left(\frac{1}{n_e^2} - \frac{1}{n_{o1}^2}\right)}$$

$$\delta\left(\frac{1}{n_{o2}^2}\right) = \frac{\frac{r_{41}^2}{2} E_x^2 \left(\frac{1}{n_{o1}^2} - \frac{1}{n_{o2}^2}\right)}{\frac{r_{41}^2}{2} E_x^2 - \left(\frac{1}{n_{o1}^2} - \frac{1}{n_{o2}^2}\right)\left(\frac{1}{n_e^2} - \frac{1}{n_{o2}^2}\right)} \cong \frac{\frac{r_{41}^2}{2} E_x^2}{\left(\frac{1}{n_e^2} - \frac{1}{n_{o2}^2}\right)}$$

$$\delta\left(\frac{1}{n_e^2}\right) = \frac{\frac{r_{41}^2}{2} E_x^2 \left(\frac{1}{n_{o2}^2} + \frac{1}{n_{o1}^2} - \frac{2}{n_e^2}\right)}{\frac{r_{41}^2}{2} E_x^2 - \left(\frac{1}{n_{o1}^2} - \frac{1}{n_e^2}\right)\left(\frac{1}{n_{o2}^2} - \frac{1}{n_e^2}\right)}$$

It can be seen that the corrections to $$\delta\left(\frac{1}{n_{o1}^2}\right); \delta\left(\frac{1}{n_{o2}^2}\right)$$

is proportional to $$\frac{r_{41}^2}{2} E_x^2$$

which is very small compare to $r_{63} E_y$ which is the correction to $n_o$, so $E_x$ should not disturb the lens.

FIG. 9 shows the phase retardation for the potentials shown in FIG. 12 for a 10 mm long crystal.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An inspection system, comprising:
   a sensor;
   a mechanical module arranged to alter a distance between an inspected object and the sensor at a rate that is lower than a first rate;
   a first focusing unit arranged to receive a first beam and to apply a first focusing function along a first direction to provide a second beam, wherein the first focusing unit is arranged to alter the first focusing function at a rate that exceeds the first rate; and
   a traveling lens acousto-optic device arranged to generate a plurality of traveling lenses in response to radio frequency signals, wherein each traveling lens of the plurality of traveling lenses is arranged to receive at least a portion of the second beam and to apply a second focusing function along a second direction to generate a plurality of focused spots and the traveling lens acousto-optic device is arranged to alter the second focusing function at a rate that exceeds the first rate; and
   optics arranged to direct the plurality of focused spots on the inspected object and to direct radiation from the inspected object to the sensor.

2. The system according to claim 1, wherein the first focusing unit is arranged to apply a third focusing function along a third direction that is substantially normal to the first direction, and wherein when the first focusing function focuses the second beam along the first direction, the third focusing function defocuses the second beam along the third direction.

3. The system according to claim 1, wherein the first focusing unit comprises one of: a core made of an ultra violet durable material, or a core made of a material that is selected from a list consisting of: Potassium Di-deuterium Phosphate, $KH_2PO_4$, Ammonium Dihydrogen Phosphate and Silicone DiOxide.

4. The system according to claim 1, wherein the first focusing unit comprises a core made of a crystal that lacks a center of symmetry.

5. The system according to claim 1, wherein refractive indexes of the core are responsive to an electric field applied on the core.

6. The system according to claim 5, wherein the first focusing unit further comprises electrodes, wherein the electrodes are arranged to induce an electrical field having a magnitude that has a substantially parabolic shape along the first direction.

7. The system according to claim 5, wherein the first focusing unit further comprises sets of electrodes, wherein one set of electrodes is arranged to induce an electrical field having a magnitude that has a parabolic shape along the first direction and wherein a second set of electrodes is arranged to induce an electrical field having a magnitude that has an inverted parabolic shape along the first direction.

8. The system according to claim 5, wherein the first focusing unit further comprises sets of electrodes; wherein one set of electrodes is arranged to induce an electrical field having a magnitude along the first direction that increases with proximity to a center of the core, and a second set of electrodes is arranged to induce an electrical field having a magnitude along the first direction that decreases with proximity to the center of the core.

9. The system according to claim 5, wherein the first focusing unit further comprises electrodes, wherein the electrodes are arranged to induce an electrical field that causes the core to act as a positive lens along the first direction and to act as a negative lens along a third direction.

10. The system according to claim 5, wherein the first focusing unit further comprises electrodes, wherein the electrodes are arranged to induce an electrical field that causes the core to act as a negative lens along the first direction and to act as a positive lens along a third direction.

11. The system according to claim 5, wherein the first focusing unit further comprises two sets of electrodes that are positioned on two facets of the core that are opposite to each other.

12. The system according to claim 1, further comprising a cylindrical lens for applying a constant focusing function along a third direction.

13. The system according to claim 1, further comprising a beam shaper, for shaping the first beam so that when arriving to the first focusing unit a width of a cross section of the first beam along the first direction is narrower than a length of the cross section of the first beam along a third direction.

14. The system according to claim 13, wherein the beam shaper is arranged to shape the first beam so that the cross section of the first beam has an elliptical shape.

15. The system according to claim 13, wherein the beam shaper is arranged to focus the first beam onto the first focusing unit; wherein the system further comprises a collimating lens that is positioned between the first focusing unit and the traveling lens acousto-optic device.

16. The system according to claim 1, wherein the first focusing unit comprises a mirror, and the first focusing unit is arranged to alter the first focusing function by moving the mirror.

17. A method for focus correction, the method comprising:
receiving a desired focus error correction measure; and
altering, at a rate that exceeds a first rate and in response to the desired focus error correction measure, at least one focusing function out of a first focusing function and a second focusing function;
wherein the first rate is faster than a rate of distance alteration applied by a mechanical module arranged to alter the distance between an inspected object and a sensor, the first focusing function is applied along a first direction by a first focusing unit, and the second focusing function is applied by a traveling lens acousto-optic device that is arranged to generate a plurality of traveling lenses in response to radio frequency signals, each of the traveling lenses arranged to receive at least a portion of the second beam and to apply the second focusing function along a second direction to generate a plurality of focused spots.

18. A method, comprising:
altering, by a mechanical module, a distance between an inspected object and a sensor at a rate that is lower than a first rate;
receiving, by a first focusing module, a first beam and applying a first focusing function along a first direction to provide a second beam;
generating, by a traveling lens acousto-optic device, a plurality of traveling lenses in response to radio frequency signals;
receiving, by each traveling lens of the plurality of traveling lenses, at least a portion of the second beam;
applying, by each traveling lens of the plurality of traveling lenses, a second focusing function along a second direction to generate a plurality of focused spots;
directing the plurality of focused spots on an inspected object;
directing radiation from the inspected object to a sensor;
sensing radiation that impinges on the sensor;
altering the first focusing function at a rate that exceeds the first rate; and
altering the second focusing function at a rate that exceeds the first rate.

* * * * *